United States Patent [19]

Sekiguchi et al.

[11] Patent Number: 4,579,687
[45] Date of Patent: Apr. 1, 1986

[54] PROCESS FOR PRODUCING SALT OF ALPHA-SULFO FATTY ACID ALKYL ESTER

[75] Inventors: Shizuo Sekiguchi, Funabashi; Katsumasa Nagano, Ichikawa; Kyozo Kitano, Narashino, all of Japan

[73] Assignee: Lion Corporation, Tokyo, Japan

[21] Appl. No.: 561,396

[22] Filed: Dec. 14, 1983

[30] Foreign Application Priority Data

Dec. 27, 1982 [JP] Japan .................... 57-234802

[51] Int. Cl.$^4$ .......................... C07C 143/90
[52] U.S. Cl. ............................. 260/400
[58] Field of Search ..................... 260/400

[56] References Cited

U.S. PATENT DOCUMENTS 3,159,657 12/1964 Wulff et al. ............ 260/400
3,354,187 11/1967 Stein et al. ............ 260/400

FOREIGN PATENT DOCUMENTS 999300 7/1965 United Kingdom ......... 260/400

*Primary Examiner*—J. E. Evans
*Attorney, Agent, or Firm*—Armstrong, Nikaido, Marmelstein & Kubovcik

[57] ABSTRACT

A process for producing the salt of an alpha-sulfo fatty acid alkyl ester having the general formula (I):

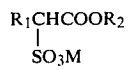

$$R_1CHCOOR_2 \atop | \atop SO_3M \qquad (I)$$

wherein $R_1$ is an alkyl or alkenyl group having 6 to 20 carbon atoms, $R_2$ is an alkyl or alkenyl group having 2 to 8 carbon atoms, and M is an alkali metal, an alkaline earth metal, ammonium, or an organic base comprising the steps of:

sulfonating a fatty acid alkyl ester having the general formula (II):

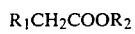

$$R_1CH_2COOR_2 \qquad (II)$$

wherein $R_1$ and $R_2$ are the same as defined above; neutralizing the sulfonated product; and
decomposing a sulfonic acid anhydride having the general formula (III):

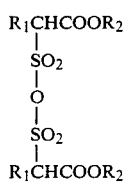

$$\begin{array}{c} R_1CHCOOR_2 \\ | \\ SO_2 \\ | \\ O \\ | \\ SO_2 \\ | \\ R_1CHCOOR_2 \end{array} \qquad (III)$$

wherein $R_1$ and $R_2$ are the same as defined above, contained in the reaction mixture. Thus, the desired salt of an alpha-sulfo fatty acid alkyl ester can be produced at a high yield from a fatty acid alkyl ester having an ester-bonded alkyl group with 2 or more carbon atoms.

4 Claims, No Drawings

PROCESS FOR PRODUCING SALT OF ALPHA-SULFO FATTY ACID ALKYL ESTER

BACKGROUND OF THE INVENTION

1. Field of the Invention

The present invention relates to a process for producing the salt of an alpha-sulfo fatty acid alkyl ester. More specifically, it relates to a process for producing the salt of an alpha-sulfo fatty acid ester from a fatty acid alkyl ester having an ester-bonded alkyl group having 2 to 8 carbon atoms at a high yield.

2. Description of the Prior Art

The salts of alpha-sulfo fatty acid alkyl esters can be generally produced by sulfonating starting fatty acid alkyl esters followed by neutralization of the resultant sulfonated products. However, since cleavage of the ester linkages or discoloration of the reaction products tends to occur during the sulfonation of fatty acid alkyl esters, several attempts have been made to prevent or suppress the cleavage of the ester linkages or discoloration of the reaction products. For example, U.S. Pat. No. 3,251,868 discloses a sulfonation process in which the starting ester is first sulfonated at a temperature of less than 70° C. by dissolving therein the total of $SO_3$ necessary to sulfonate the starting ester to such an extent that approximately half the amount of the ester is sulfonated and, then, the sulfonation is completed at a temperature of 70° C. or more. Japanese Unexamined Patent Publication (Kokai) No. 57-126895 discloses a sulfonation process in which the starting ester is previously purified, to remove impurities contained therein, before the sulfonation. Furthermore, British Patent Specification No. 1145101 discloses a sulfonation process in which the starting ester is sulfonated at a temperature of 100° C. to 140° C. by downwardly flowing the starting ester in the form of a film. Japanese Unexamined Patent Publication (Kokai) No. 53-2419 discloses a sulfonation process in which the starting ester is first sulfonated and the reaction mixture is aged after cooling.

These proposed processes yield the salts of alpha-sulfo fatty acid methyl esters useful as a surfactant at a relatively high yield by neutralizing the resultant sulfonated products, as long as methyl esters are used as the starting fatty acid alkyl esters. However, when fatty acid alkyl esters having an alkyl group with 2 or more carbon atoms ester-bonded to the fatty acid are used as the starting material, the yield of the salts of the alpha-sulfo fatty acid alkyl esters obtained from the neutralization of the sulfonated products of the above-mentioned conventional processes is very low. Since the salts of alpha-sulfo fatty acid alkyl esters having an alkyl group with 2 or more carbon atoms have a surface active function (or detergency) identical to or greater than that of the salts of alpha-sulfo fatty acid methyl esters, the salts of the alpha-sulfo fatty acid alkyl esters having an alkyl group with 2 or more carbon atoms are useful surfactants comparable to the salts of alpha-sulfo fatty acid methyl esters. Thus, it is desirable to obtain the salts of alpha-sulfo fatty acid alkyl esters having an alkyl group with 2 or more carbon atoms at a high yield.

SUMMARY OF THE INVENTION

Accordingly, the objects of the present invention are to eliminate the above-mentioned problems in the prior art and to provide a process for producing the salt of an alpha-sulfo fatty acid ester from a fatty acid alkyl ester having an ester-bonded alkyl group having 2 to 6 carbon atoms at a high yield.

Other objects and advantages of the present invention will be apparent from the following description.

In accordance with the present invention, there is provided a process for producing the salt of an alpha-sulfo fatty acid alkyl ester having the general formula (I):

wherein $R_1$ is an alkyl or alkenyl group having 6 to 20 carbon atoms, $R_2$ is an alkyl or alkenyl group having 2 to 8 carbon atoms, and M is an alkali metal, an alkaline earth metal, ammonium, or an organic base comprising the steps of:

sulfonating a fatty acid alkyl ester having the general formula (II):

wherein $R_1$ and $R_2$ are the same as defined above;
neutralizing the sulfonated product; and
decomposing a sulfonic acid anhydride having the general formula (II):

wherein $R_1$ and $R_2$ are the same as defined above, contained in the reaction mixture.

DESCRIPTION OF THE PREFERRED EMBODIMENT

The present inventors have discovered as a result of investigations that the above-mentioned low yield of the salts of alpha-sulfo fatty acid $C_2+$ alkyl esters ("$C_2+$ alkyl" herein means alkyl groups having 2 or more carbon atoms) is not caused by the sulfonation and neutralization conditions, but is caused by the formation of sulfonic acid anhydride as a by-product. That is, when fatty acid $C_2+$ alkyl esters are sulfonated, about 20% of sulfonic acid anhydride is unavoidably produced as a by-product during the sulfonation, unlike the sulfonation of fatty acid $C_1+$ alkyl esters (i.e., fatty acid methyl esters). The inventors have found, based on this elucidation, that the sulfonic acid anhydride formed as a by-product can be decomposed into the salts of alpha-sulfo fatty acid $C_2+$ alkyl esters by heating the sulfonation reaction mixture after neutralization, whereby the yield of the desired salts of alpha-sulfo fatty acid $C_2+$ alkyl esters can be increased. The occurrence of similar phenomena has been confirmed in the case of fatty acid alkenyl esters.

The fatty acid alkyl esters having the above-mentioned general formula (II) used as the starting material in the present invention include, for example, those which are derived from fatty acids having 8 to 22 carbon atoms and alcohols having 2 to 8 carbon atoms. Either linear or branched fatty acid esters can be used in the present invention. Examples of the typical fatty acid esters are ethyl esters, propyl esters, butyl esters, pentyl esters, hexyl esters, isopropyl esters, and isobutyl esters, of tallow fatty acids, palm fatty acids, palm kernel fatty acids, fish fatty acids, synthetic fatty acids, and oleic acid. These fatty acid esters can be used alone or in any mixture thereof.

The sulfonation of the starting fatty acid alkyl esters can be carried out by using similar sulfonating agents and sulfonating apparatus under similar sulfonating conditions as in the case of fatty acid methyl esters. Generally, the sulfonation is carried out by using $SO_3$ gas as a sulfonating agent at a mole ratio of $SO_3$ to the starting fatty acid esters of 1.0 to 2.0 and a temperature of more than the solidification point of the starting esters but not more than 150° C. in a film type or vessel type reactor. After the sulfonation reaction, the reaction mixture can be optionally aged, for example, at a temperature of 50° C. to 100° C. for 5 to 120 minutes.

As mentioned above, about 20% of the sulfonic acid anhydride having the above-mentioned general formula (III), which is not formed in the sulfonation of fatty acid methyl esters, is unavoidably produced as a by-product during the sulfonation in the present invention. Thus, a considerable amount of sulfonic acid anhydride is present as a contaminant in the sulfonation reaction products. When a small amount of sulfonic acid anhydrides is present in the sulfonation reaction mixtures as in the case of alkylbenzenes being sulfonated, the sulfonic acid anhydrides can be converted into sulfonic acids by hydrolyzing the sulfonation reaction mixtures in the presence of water. However, when a relatively large amount of sulfonic acid anhydrides is present in the sulfonation reaction mixture as in the present invention, the viscosity of the sulfonation reaction mixture is increased by the addition of water and, therefore, the hydrolysis efficiency is remarkably decreased. Thus, according to the present invention, the sulfonation reaction mixtures are neutralized after optional bleaching and the sulfonic-acid anhydrides contained in the neutralized reaction mixture are then hydrolyzed.

The bleaching of the sulfonation reaction mixtures is not necessarily required in the present invention. If bleaching, the sulfonation reaction mixtures can be preferably bleached, at a temperature of 50° C. to 120° C. for 1 to 120 minutes while stirring, by using 0.1% to 10% by weight of a peroxide type bleaching agent such as hydrogen peroxide in the presence of 0% to 30% by weight of a $C_1$ to $C_{10}$ fatty alcohol and 0% to 30% by weight of water (all based on the total weight of the sulfonated products).

The sulfonation reaction mixtures, after being optionally subjected to bleaching treatment, are neutralized. The neutralization can be carried out in any conventional manner, for example, by adding an aqueous or alcoholic solution of alkali metal hydroxides, alkaline earth metal hydroxides, ammonia, monoethanol amine, diethanol amine, triethanol amine, and the like to the sulfonation reaction mixture, followed by stirring. It should be noted that the alkali metal hydroxides or the other neutralizing agents are used in an amount sufficient to neutralize the alpha-sulfo fatty acid esters which are already present in the sulfonation reaction mixture, and to neutralize the alpha-sulfo fatty acid alkyl esters which will be converted from the sulfonic acid anhydrides in the subsequent step.

The neutralized reaction mixture obtained from the neutralization step is then subjected to the decomposition of the sulfonic acid anhydrides contained in the reaction mixture. The decomposition of the sulfonic acid anhydrides contained in the reaction mixture can be carried out by allowing the reaction mixture to stand at an ambient temperature. However, in order to accelerate the decomposition rate, the decomposition of the sulfonic acid anhydrides is preferably carried out by heating the reaction mixture, for example, at a temperature of 40° C. to 150° C., more preferably 50° C. to 150° C. for 1 to 120 minutes, while stirring. In this way, the sulfonic acid anhydrides contained in the neutralized reaction mixture are decomposed and then neutralized to yield the salts of alpha-sulfo fatty acid alkyl esters. Thus, according to the present invention, the increase in the yield of the desired products, the salts of alpha-sulfo fatty acid alkyl esters, can be accomplished.

As is clear from the above-mentioned description, the inventors have discovered as a result of investigations that the salts of alpha-sulfo fatty acid $C_2^+$ alkyl esters having excellent surface active functions comparable to the salts of alpha-sulfo fatty acid $C_1^+$ alkyl esters can be obtained only in a small amount according to any conventional process and the inventors have proposed a process in which the salts of alpha-sulfo fatty acid $C_2^+$ alkyl esters can be prepared at a high yield. Thus, the present invention is very effective from the standpoint of commercialization. Although the detailed mechanism cannot be clearly understood, it is believed that the sulfonic acid anhydrides which are not formed in the sulfonation of fatty acid methyl esters are produced as a by-product due to steric hindrance of alkyl groups ester-bonded to the fatty acids when fatty acid $C_2^+$ alkyl esters are sulfonated.

EXAMPLE

The present invention now will be further illustrated by, but is by no means limited to, the following examples, in which all percentages are expressed on a weight basis unless otherwise specified.

EXAMPLE 1

A 300 g amount of extremely hardened palm fatty acid ethyl ester having an average molecular weight of 300 and an I.V. of 0.05 was charged into a 1 liter separable flask and heated to a temperature of 80° C. In the flask, 120 g (1.5 mole) of $SO_3$ diluted with nitrogen gas to 5% by volume was introduced into the ester for 60 minutes while stirring, whereby the fatty acid ethyl ester was sulfonated. The resultant sulfonation reaction mixture was divided into four portions. The four portions (100 g each) of the reaction mixture thus obtained were separately placed into 300 ml Erlenmeyer flasks and were treated under the following experimental conditions A, B, C, and D.

Experiment A: A 15% amount of ethanol and 2% of $H_2O_2$ (based on the weight of the sulfonated products) were added to a 100 g amount of the sulfonation reaction mixture, and the sulfonation reaction mixture was bleached at a temperature of 80° C. for 60 minutes. Then, the resultant reaction mixture was neutralized at a pH of 6 to 7 by adding 10% of an aqueous caustic soda solution thereto.

Experiment B: The experiment A was repeated, except that 10% of water was added to the reaction mixture and was heated at a temperature of 50° C. for 20 minutes prior to the bleaching and neutralization.

Experiment C: The experiment A was repeated, except that 10% of water was added to the reaction mixture when the sulfonation reaction mixture was bleached.

Experiment D: The reaction mixture was heated at a temperature of 80° C. for 30 minutes after the reaction mixture was treated in the same manner as in experiment A.

The petroleum ether extracts including the unreacted oil and the sulfonic acid anhydrides, the colors, and the contents of the salts of alpha-sulfo fatty acids of the reaction mixtures obtained above were determined. The results are shown in Table 1 below.

TABLE 1

| Experiment No. | A | B | C | D |
|---|---|---|---|---|
| Petroleum ether extract*[1] | | | | |
| (1) Sulfonic acid anhydride (based on AI %)*[2] | 14.2 | 3.2 | 2.8 | trace |
| (2) Starting ester (based on AI %) | 1.0 | 1.0 | 1.0 | 1.0 |
| Color (5% aqueous solution)*[3] | 50 | 110 | 70 | 30 |
| Content of salt of alpha-sulfo fatty acid*[4] | 17 | 27 | 35 | 17 |

*[1]: The reaction mixture was extracted three times with petroleum ether.
*[2]: The petroleum ether extract was hydrolyzed by ethanol-NaOH and then the content of the sulfonate was quantitatively determined by an MB method. (AI = surfactant content)
*[3]: Determined by means of a Klett Summerson spectrophotometer (10 mm × 40 m cell).
*[4]: A 90% ethanol undissolved matter was quantitatively determined by an MB method.

As is clear from the results shown in Table 1, the amount of sulfonic acid anhydride present in the sulfonation reaction mixture was minimized to a trace amount in experiment D according to the present invention and, therefore, the desired increase in the yield of the salts of alpha-sulfo fatty acid ethyl ester was accomplished.

EXAMPLE 2

Palm fatty acid ethyl ester having an average molecular weight of 300 and an I.V. of 0.02 was sulfonated in the same manner as in Example 1 and then, the resultant sulfonation reaction mixture was bleached at a temperature of 80° C. for 60 minutes by adding 15% of ethanol and 2% of H$_2$O$_2$ (both based on the weight of the sulfonated product) thereto.

Thereafter, the resultant reaction mixture was neutralized while stirring by adding a 10% aqueous solution of triethanol amine thereto in such an amount that the pH of the reaction mixture became 6.5.

The neutralized reaction mixture thus obtained was subjected to a heat treatment under the conditions listed in Table 2. The petroleum ether extracts, the colors, and the contents of the salts of alpha-sulfo fatty acids of the reaction mixtures obtained above were determined in the same manner as in Example 1. The results are shown in Table 2.

TABLE 2

| Experiment No. | E | F | G | H |
|---|---|---|---|---|
| Heat treatment conditions: | | | | |
| Temperature (°C.) | No treatment | 60 | 120 | 30 |
| Time (min.) | No treatment | 120 | 2 | 120 |
| Petroleum ether extract (based on AI %) | 14.9 | 0.9 | 0.7 | 13.7 |
| Color (5% aqueous solution) | 55 | 35 | 21 | 55 |
| Content of salt of alpha-fatty acid | 16.8 | 17.2 | 18.5 | 16.9 |

As is clear from the results shown in Table 2, according to the present invention, desirable results could be obtained when the sulfonation reaction mixtures were heat-treated at a temperature of 50° C. to 150° C. for 1 to 120 minutes.

We claim:

1. A process for producing the salt of an alpha-sulfo fatty acid alkyl ester having the formula (I);

wherein R$_1$ is an alkyl or alkenyl group having 6 to 10 carbon atoms, R$_2$ is an alkyl or alkenyl group having 2 to 8 carbon atoms, and M is an alkali metal, an alkaline earth metal, ammonium, or an organic base comprising the steps of:

(1) sulfonating a fatty acid alkyl ester having the formual (II):

wherein R$_1$ and R$_2$ are the same as defined above, to form a mixture comprising the product (I) and a by-product suflonic anhydride having the formual (III):

wherein R$_1$ and R$_2$ are the same as defined above;

(ii) neutralizing said mixture to a pH of 6–7; and
(iii) decomposing the sulfonic acid anhydride by heating said neutralized mixture having a pH 6–7 until the content of sulfonic anhydride remaining in the mixture is less than 2.8% by weight, as determined by petroleum ether extraction.

2. A process as claimed in claim 1, wherein the decomposition of the sulfonic acid anhydride is carried out at a temperature of 40° C. to 150° C.

3. A process as claimed in claim 1, wherein the decomposition of the sulfonic acid anhydride is carried out at a temperature of 50° C. to 150° C. for 1 to 120 minutes.

4. A process as claimed in claim 1, wherein the content of sulfonic anhydride remaining in the mixture is a trace amount.

* * * * *